United States Patent [19]
Lajoie

[11] Patent Number: 5,466,470
[45] Date of Patent: Nov. 14, 1995

[54] CO-MICRONIZED BICARBONATE SALT COMPOSITIONS

[75] Inventor: M. Stephen Lajoie, Basking Ridge, N.J.

[73] Assignee: Church & Dwight Co., Inc., Princeton, N.J.

[21] Appl. No.: 248,686

[22] Filed: May 25, 1994

Related U.S. Application Data

[62] Division of Ser. No. 90,957, Jul. 13, 1993, Pat. No. 5,424,077.

[51] Int. Cl.⁶ .......................... A01N 59/16; A01N 59/00; A01N 25/08

[52] U.S. Cl. .......................... 424/641; 424/405; 424/409; 424/489; 424/600; 424/617; 424/635; 424/642; 424/643; 424/650; 424/688; 424/691; 424/692; 424/715; 424/716; 424/717; 424/722; 424/724; 514/769; 514/951

[58] Field of Search ..................... 424/641, 642, 424/643, 489, 405, 409, 717, 716, 600, 617, 635, 650, 688, 691, 692, 715, 722, 724; 514/951, 769; 241/22, 5, 30; 71/DIG. 1; 504/119, 120

[56] References Cited

U.S. PATENT DOCUMENTS

| | | | |
|---|---|---|---|
| 2,069,710 | 2/1937 | Missbach | 424/641 |
| 4,650,126 | 3/1987 | Feder et al. | 241/22 |
| 4,851,421 | 7/1989 | Iwasaki et al. | 514/352 |
| 4,880,169 | 11/1989 | Zander et al. | 241/5 |

OTHER PUBLICATIONS

Perry's Chemical Engineers' Handbook, 6th ed., McGraw-Hill Book Co., New York, 1984, pp. 8–14.

*Primary Examiner*—Glennon H. Hollrah
*Assistant Examiner*—John D. Pak
*Attorney, Agent, or Firm*—Charles B. Barris

[57] ABSTRACT

This invention provides a co-micronized bicarbonate salt composition which is a blend of ingredients having a particle size between about 0.01–1.0 micron. The composition is produced by mill co-micronization of a crystalline bicarbonate ingredient and a crystalline inorganic compound ingredient having a Mohs hardness value between about 3–7. A co-micronized blend such as sodium bicarbonate and zinc oxide is free-flowing and essentially free of agglomerated particles.

5 Claims, No Drawings

CO-MICRONIZED BICARBONATE SALT COMPOSITIONS

This application is a division of application Ser. No. 08/090,957, filed Jul. 13, 1993 which is now U.S. Pat. No. 5,424,077.

BACKGROUND OF THE INVENTION

It is known that the physicochemical properties of solids in particulate form are influenced by the size and shape of the particles. As particle size of solids diminishes in scale, there is an enhancement of properties, and often the inception of new properties. Investigators are finding that nanostructural materials can exhibit unique mechanical, electronic and optical properties.

New commercial products are becoming available which provide special advantage because of fine particle size. Zinc oxide is widely utilized as an ingredient in human health products. Superior results are now obtained by the use of submicron transparent zinc oxide powder. The ultrafine zinc oxide provides advantage for UVA/B-protection in cosmetic formulations, and exhibits enhanced antimicrobial capacity and functions as a preservative.

Alkali metal bicarbonate is another commodity reagent which has found application in a broad variety of products such as laundry detergents, deodorizers, creams and lotions, dentifrices, antacids, buffers, fungicides, and the like.

There is evidence that fine particle size alkali metal bicarbonate or ammonium bicarbonate can exhibit increased reactivity in comparison with coarse grain bicarbonate salts. In soda cracker production, finely divided sodium bicarbonate ingredient is more efficiently distributed and effectively reactive during the cracker dough preparation. The finished baked cracker is an improved product which has a substantially uniform texture, flavor and surface color, and a consistent pH throughout.

The inclusion of particulate alkali metal bicarbonate in an antiperspirant-deodorant cosmetic stick provides a product with improved deodorant properties. However, coarse grains alkali metal bicarbonate has an undesirable tendency to settle in an antiperspirant-deodorant cosmetic stick matrix. The use of ultrafine alkali metal bicarbonate as a deodorant ingredient in cosmetic stick and roll-on type personal care products is being investigated, since the ultrafine particles have less tendency to settle than coarse grain particles when dispersed in a liquid or semi-solid matrix.

A limiting factor has been the unavailability of alkali metal bicarbonate or ammonium bicarbonate powder which is composed of free-flowing ultrafine particles that are not in an agglomerated state.

There is continuing interest in the development of reagents such as alkali metal bicarbonate and ammonium bicarbonate which have an ultrafine particle size, and exhibit a novel combination of properties when utilized as an ingredient in personal care, biologically active, household, and specialty type products.

Accordingly, it is an object of this invention to provide particulate alkali metal bicarbonate and ammonium bicarbonate having an ultrafine particle size, and a surface area of at least about ten square meters per gram.

It is another object of this invention to provide alkali metal and ammonium bicarbonate powder having a submicron particle size, and which is free-flowing and essentially free of agglomerated particles.

It is a further object of this invention to provide a process for producing an ultrafine bicarbonate salt composition which is a co-micronized blend of crystalline compounds having a submicron particle size range.

Other objects and advantages of the present invention shall become apparent from the accompanying description and examples.

Publications of background interest with respect to the present invention subject matter include U.S. Pat. Nos. 2,378,147; 3,241,977; 4,997,454; and 5,147,631.

DESCRIPTION OF THE INVENTION

One or more objects of the present invention are accomplished by the provision of a co-micronized bicarbonate salt composition comprising (1) at least one crystalline compound ingredient selected from alkali metal and ammonium bicarbonates, and (2) between about 10–50 weight percent of at least one crystalline inorganic compound ingredient having a Mohs hardness value between about 3–7; wherein the crystalline ingredients of the composition have an average particle size in the range between about 0.01–1.0 micron as obtained by mill co-micronization of the crystalline ingredients.

In another embodiment this invention provides a process for producing a co-micronized bicarbonate salt composition which comprises (1) blending ingredients comprising (a) at least one crystalline compound selected from alkali metal and ammonium bicarbonates, and (b) between about 10–50 weight percent of at least one crystalline inorganic compound having a Mohs hardness value between about 3–7; and (2) milling the blend to co-micronize the ingredients to an average particle size in the range between about 0.01–1.0 micron.

A present invention composition comprises a physical blend of ultrafine particles of the crystalline ingredients, and the particles characteristically are in an unagglomerated form, and the composition has free-flowing properties.

The terms "average particle size" and "average diameter" as employed herein refers to the average of the largest dimension of particles.

The bicarbonate ingredient of an invention composition is sodium bicarbonate, potassium bicarbonate, ammonium bicarbonate, or any mixture thereof.

The inorganic ingredient is at least one compound having a Mohs hardness value between about 3–7. The inorganic compound ingredient is selected to have a Mohs hardness which is higher than the 2–3.5 Mohs hardness value of the alkali metal or ammonium bicarbonate ingredient.

Inorganic carbonates normally have an average Mohs value of about 3–4, inorganic silicates have an average Mohs value of about 5–6, and inorganic oxides have an average Mohs value of about 5–7.

Suitable inorganic compounds for purposes of the present invention compositions include calcium carbonate, copper carbonate, zinc carbonate, barium carbonate, magnesium carbonate, manganese carbonate, calcium silicate, magnesium silicate, copper silicate, manganese silicate, titanium dioxide, tin oxide, zinc oxide, silicon oxide, aluminum oxide, magnesium oxide, copper oxide, zirconium oxide, beryllium oxide, calcium fluoride, zinc sulfide, aluminum phosphate, and the like.

A present invention co-micronized bicarbonate salt composition exhibits novel properties which are derived from the particular method of preparation, i.e., a crystalline bicarbonate salt compound is mill co-micronized with a crystalline inorganic compound having a Mohs hardness value between about 3–7.

If an alkali metal or ammonium bicarbonate salt as a sole ingredient is subjected to a mill micronization procedure, the resultant ultrafine powder tends to be in the form of cohesive agglomerated crystallites of primary particles, and the powder is not free-flowing. The agglomerated crystallites may have an average diameter between about 1–10 microns, and higher.

In accordance with the present invention, a crystalline bicarbonate salt ingredient is mill co-micronized with a crystalline inorganic compound to yield a co-micronized composition which has an average particle size diameter in the range between about 0.01–1.0 micron. A present invention co-micronized bicarbonate salt composition is free-flowing and essentially free of agglomerated primary particles.

The presence of a crystalline compound ingredient during a co-micronization procedure provides at least two advantages.

First, the crystalline inorganic compound ingredient serves as a grinding medium because of its particle hardness, and the average size of the bicarbonate salt particles is reduced into a submicron range.

Second, the presence of the ultrafine crystalline inorganic compound particles in a co-micronized powder composition inhibits agglomeration of the ultrafine bicarbonate salt particles, and the co-micronized powder is free-flowing.

A present invention co-micronized bicarbonate salt composition can be prepared by means of a grinding, impact or fluid energy type of milling equipment which is designed to micronize crystalline solids to ultrafine powders.

One type of mill involves the use of rollers or balls in combination with an annular grinding plate, such as bowl roll mills, roller mills and ring-ball mills. Another type of mill involves the use of a pulverizing rotor. These types of mills are illustrated in U.S. Pat. Nos. 2,253,839; 4,550,879; 4,562,972; 4,566,639; 4,919,341; and references cited therein.

Fluid energy jet mills have found application for the comminution of a wide variety of particulate solids. Jet mills are well adapted to micronize and particle size classify particulate solids into ultrafine powders. An important application is the micronization of pigments such as titanium dioxide.

Fluid energy jet mills are size reduction machines in which particles to be ground are accelerated in a stream of gas, (e.g., compressed air) and micronized in a grinding chamber by their impact against each other or against a stationary surface in the grinding chamber. Different types of fluid energy mills can be categorized by their particular mode of operation. Mills may be distinguished by the location of feed particles with respect to incoming air. In the commercially available Majac jet pulverizer (Majac Inc.), particles are mixed with the incoming gas before introduction into the grinding chamber. In the Majac mill, two streams of mixed particles and gas are directed against each other within the grinding chamber to cause fracture. An alternative to the Majac mill configuration is to accelerate within the grinding chamber particles that are introduced from another source, such as a mill with an annular grinding chamber into which numerous gas jets inject pressurized air tangentially (U.S. Pat. No. 3,565,348).

During jet mill grinding, particles that have reached the desired size are separated, while the remaining coarser particles continue to be ground. The particle size classification process can be accomplished by the circulation of the gas and particle mixture in the grinding chamber. In pancake type mills, the gas is introduced around the periphery of the cylindrical grinding chamber to induce a vorticular flow within the chamber. Coarser particles tend to the periphery where they are ground further, while finer particles migrate to the center of the chamber where they are drawn off into a collector outlet located in proximity to the grinding chamber.

Particle size classification can also be accomplished by a separate classifier. This type of classifier is mechanical and features a rotating vaned cylindrical rotor. The air flow from the grinding chamber only can force particles below a certain size through the rotor against the centrifugal forces imposed by the rotor's speed. These particles are the mill's micronized product. Oversized particles are returned to the grinding chamber.

Variation in fluid energy jet mill design are illustrated in U.S. Pat. Nos. 4,219,164; 4,261,521; 4,280,664; 4,526,324; 4,602,743; 4,638,953; 4,664,319; 4,811,907; 4,880,169; 4,962,893; 4,133,504; and references cited therein.

A present invention co-micronized bicarbonate salt composition exhibits a novel combination of properties because of its free-flowing ultrafine particle size when utilized as an ingredient in personal care and specialty type products.

The inclusion of a present invention submicron bicarbonate salt powder as an ingredient enhances odor absorption and neutralization in personal care products, such as those adapted for skin care, oral care or feminine hygiene usage.

A present invention submicron bicarbonate salt powder as an ingredient provides improved esthetics in creams, lotions, gels, ointments, soapbars, toothpastes, and the like. Irritation is minimized, skin mildness is improved, and antibacterial/antifungal activity is increased.

Another valuable property of a present invention co-micronized bicarbonate salt composition is an exceptional capability to blend readily into suspension formulations with other ingredients. The ultrafine size and high surface area of the particles facilitate the formation of a homogenous solid-phase suspension in a liquid medium which has long term stability. A present invention co-micronized bicarbonate salt composition can have a specific surface area (BET) between about 10–60 meters per gram.

A particularly preferred co-micronized composition of the present invention is a physical admixture of ultrafine crystalline sodium bicarbonate and/or potassium bicarbonate with between about 10–40 weight percent of ultrafine crystalline zinc oxide. This type of composition can exhibit enhanced bicarbonate fungicidal activity, and enhanced zinc oxide fungicidal and bactericidal activities because of submicron particle size.

A present invention composition can consist of three or more ingredients, such as a co-micronized blend of sodium bicarbonate, magnesium carbonate and calcium silicate.

Standard procedures are followed for measurement of the physical properties of the ultrafine particles in an invention co-micronized composition.

Surface area is determined by the nitrogen absorption method of Brunauer, Emmett and Teller (BET) as described in J.A.C.S., 60, 309 (1938).

Particle size is determined by transmission electron microscopy, or by X-ray diffractometry.

In a further embodiment this invention contemplates a submicron particle size zinc oxide powder composition which remains unagglomerated and free-flowing for an extended storage period. The free-flowing zinc oxide powder has a content of about 2–20 weight percent of at least one crystalline inorganic compound having an average particle size between about 0.01–20 microns. Pure zinc oxide powder of about 0.01–1 micron average particle size tends to agglomerate into larger particles after standing for three months or more under ambient storage conditions.

The following examples are further illustrative of the present invention. The components and specific ingredients are presented as being typical, and various modifications can be derived in view of the foregoing disclosure within the scope of the invention.

EXAMPLE I

This Example illustrates a prior art method of preparing microparticles of sodium bicarbonate.

A saturated solution of sodium bicarbonate in water is prepared. The solution is added dropwise to a stirred volume of cold methanol solvent, until 10% by volume has been admixed. The resultant crystalline precipitate is collected by filtration, and dried under vacuum at 60° C.

The primary acicular particles have a length of about 1–2 microns, and are in the form of agglomerated crystallite particles having a diameter of about 5–8 microns, and a surface area of about 4 square meters per gram. The agglomerated particles are not free-flowing.

If the methanol solvent is added dropwise to the saturated sodium bicarbonate solution with stirring, the primary crystallite and agglomerated crystallite particles of the recovered crystalline precipitate are larger in dimensions as compared to the product of the first precipitation procedure described above.

EXAMPLE II

This Example illustrates the preparation of a present invention co-micronized sodium bicarbonate/zinc oxide composition by air-jet milling.

Air-jet pulverized sodium bicarbonate is commercially available (Particle Size Technology, Inc.). The commercial sodium bicarbonate has an average particle size of about 5 microns, and 90 percent of the particles have a diameter less than 20 microns. The sodium bicarbonate is substantially in the form of crystallites of agglomerated primary particles which are not free-flowing.

In accordance with the present invention, air-jet milling equipment (similar to that in U.S. Pat. No. 4,880,169) is employed to prepare a free-flowing co-micronized composition consisting of 70 weight percent of sodium bicarbonate and 30 weight percent of zinc oxide. The co-micronized composition has an average particle size in the range of 0.05–1.0 micron, and 90 percent of the particles have a diameter less than 0.5 micron. The co-micronized composition is unagglomerated and free-flowing.

The sodium bicarbonate starting material has an average particle size of about 50 microns. The zinc oxide starting material has an average particle size of about 10 microns, and a Mohs hardness value of about 4.

The procedure described above is repeated, except that magnesium oxide is substituted for the zinc oxide. The magnesium oxide has a Mohs hardness value of about 6. The sodium bicarbonate/magnesium oxide powder is substantially unagglomerated and free-flowing.

If sodium bicarbonate alone is jet-milled following the above-described procedure, an agglomerated product is obtained which is not free-flowing. The average particle size of an agglomerated crystallite is about 8 microns.

EXAMPLE III

This Example illustrates a pilot-plant procedure for the preparation of an antiperspirant-deodorant cosmetic stick product which utilizes a co-micronized alkali metal bicarbonate ingredient in accordance with the present invention.

A stainless steel tank is provided which is equipped with turbine agitation.

Silicone oil DC 245 (600 lbs, Dow Corning) is charged to the mixing tank. Agitation (55–65 RPM) is initiated, and heating the liquid medium to 176° F. is commenced.

During the heating period, the following order of ingredients are added to the stirred liquid medium:

|  | lbs. |
|---|---|
| diisopropyl adipate | 60 |
| PPG 14 butyl ether (Americol) | 40 |
| stearyl alcohol | 340 |
| castor wax (MP-70) | 60 |
| eicosanol | 10 |
| PEG 600 distearate (Mazer) | 40 |

The mixture is stirred at 156° F. for about 30 minutes until the ingredients are melted and the liquid medium is homogeneous. The stirring speed is reduced to about 35 RPM, then Cab-o-sil M-5 (15 lbs, Cabot) and aluminum zirconium tetrachlorohydrex glycine (480 lbs, Reheis) are added. The temperature is maintained at 156° F. for about 40 minutes until the fluid medium is uniform, and then the temperature is lowered to 124° F.

Co-micronized sodium bicarbonate/zinc oxide powder (120 lbs) and a fragrance (6 lbs, 1FF 567-AT) respectively are added with stirring to Silicone oil DC 245 (245 lbs, Dow Corning) in a second mixing tank at a temperature of 124° F. to form a homogeneous suspension medium. The co-micronized sodium bicarbonate/zinc oxide (75/25) powder is prepared by an air-jet pulverizing method. The average particle size of the free-flowing powder is about 0.6 micron.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 7 (ASTM Method D5).

A second deodorant cosmetic stick product is prepared by eliminating the antiperspirant ingredient, and increasing the quantity of co-micronized sodium bicarbonate/zinc oxide ingredient from 120 lbs to 160 lbs in the above described manufacturing process.

EXAMPLE IV

This Example illustrates the preparation of a concentrated mouthwash formulation in accordance with the present invention.

A formulation is prepared from the following ingredients:

|  | Parts by Weight |
|---|---|
| ethanol (5% water) | 40.00 |
| sorbitol (70% in water) | 10.00 |
| glycerol | 5.00 |
| water | 25.00 |
| potassium bicarbonate/zinc oxide (60/40)[1] | 15.00 |
| pluronic F-108[2] | 2.00 |
| cetylpyridium chloride | 0.01 |
| sodium salicylate | 0.20 |
| allantoin | 0.20 |
| sodium saccharin | 0.10 |
| FDC Green 3 (2% solution) | 0.25 |
| peppermint oil | 0.20 |

[1]90% of particles in 0.05–0.5 micron particle size range; prepared by an air-jet mill procedure.
[2]polyoxypropylene polyoxyethylene condensation; BASF- Wyandotte.

A solution is formed of the ethanol, water and sorbitol ingredients. The Pluronic F-108 is added, followed by potassium bicarbonate/zinc oxide and other ingredients in the listed order with high speed stirring.

The liquid mouthwash concentrate has translucent optical clarity. The liquid medium has a clear green color when diluted with two parts of water per one part of liquid concentrate.

What is claimed is:

1. A co-micronized bicarbonate salt composition comprising (1) at least one crystalline compound ingredient selected from the group consisting of alkali metal and ammonium bicarbonates, and (2) between about 10–50 weight percent of at least one crystalline inorganic metal oxide compound ingredient having a Mohs hardness value between about 3–7; wherein the crystalline ingredients of the composition have an average particle size in the range between about 0.01–1.0 micron which is obtained by mill co-micronization of the crystalline ingredients, and the composition is free-flowing and essentially free of agglomerated particles.

2. A composition in accordance with claim 1 wherein the co-micronization is by fluid energy milling.

3. A composition in accordance with claim 1 wherein the co-micronization is by grinding or impact milling.

4. A composition in accordance with claim 1 wherein the ingredients comprise sodium bicarbonate and between about 10–40 weight percent of zinc oxide.

5. A composition in accordance with claim 1 wherein the ingredients comprise potassium bicarbonate and between about 10–40 weight percent of zinc oxide.

* * * * *